(12) United States Patent
Kojima

(10) Patent No.: US 10,821,475 B2
(45) Date of Patent: Nov. 3, 2020

(54) ULTRASONIC DEVICE AND ULTRASONIC APPARATUS

(71) Applicant: Seiko Epson Corporation, Tokyo (JP)

(72) Inventor: Chikara Kojima, Matsumoto (JP)

(73) Assignee: Seiko Epson Corporation (JP)

( * ) Notice: Subject to any disclaimer, the term of this patent is extended or adjusted under 35 U.S.C. 154(b) by 510 days.

(21) Appl. No.: 15/834,531

(22) Filed: Dec. 7, 2017

(65) Prior Publication Data
US 2018/0161816 A1  Jun. 14, 2018

(30) Foreign Application Priority Data

Dec. 9, 2016 (JP) .................................. 2016-239751

(51) Int. Cl.
*B06B 1/06* (2006.01)
*A61B 8/14* (2006.01)
(Continued)

(52) U.S. Cl.
CPC .............. *B06B 1/0629* (2013.01); *A61B 8/04* (2013.01); *A61B 8/085* (2013.01); *A61B 8/14* (2013.01); *A61B 8/4488* (2013.01); *A61B 8/54* (2013.01); *B06B 1/0622* (2013.01); *B06B 1/0692* (2013.01); *H01L 41/0533* (2013.01); *A61B 8/145* (2013.01); *A61B 8/4281* (2013.01);
(Continued)

(58) Field of Classification Search
CPC ... B06B 1/0629; B06B 1/0622; B06B 1/0692; A61B 8/04; A61B 8/085; A61B 8/14; A61B 8/4488; A61B 8/54; A61B 8/145; A61B 8/4281; A61B 8/4422; A61B 8/4427; A61B 8/4494
See application file for complete search history.

(56) References Cited

U.S. PATENT DOCUMENTS 9,308,727 B2  4/2016  Hirai et al.
9,508,916 B2  11/2016  Nakamura et al.
(Continued)

FOREIGN PATENT DOCUMENTS

JP  2010-105261 A  5/2010
JP  2014-078906 A  5/2014
(Continued)

*Primary Examiner* — J. Sam Martin
(74) *Attorney, Agent, or Firm* — Harness, Dickey & Pierce, P.L.C.

(57) ABSTRACT

An ultrasonic device includes: a substrate including a first groove portion and a second groove portion in a first surface; a vibration film provided on the first surface and closing the first groove portion and the second groove portion; a first piezoelectric element provided on the vibration film and overlapping the first groove portion in a plan view as viewed in a thickness direction of the substrate; and a second piezoelectric element provided on the vibration film and overlapping the second groove portion in the plan view. The substrate is provided with a third groove portion coupling the first groove portion to the second groove portion. The substrate is provided with a fourth groove portion extending in a direction away from the first piezoelectric element and the second piezoelectric element in the plan view and coupled to the third groove portion. A hole portion coupling a second surface of the substrate that is opposed to the first surface to the fourth groove portion is provided.

8 Claims, 13 Drawing Sheets

(51) Int. Cl.
*H01L 41/053* (2006.01)
*A61B 8/00* (2006.01)
*A61B 8/08* (2006.01)
*A61B 8/04* (2006.01)

(52) U.S. Cl.
CPC .......... *A61B 8/4422* (2013.01); *A61B 8/4427* (2013.01); *A61B 8/4494* (2013.01)

(56) References Cited

U.S. PATENT DOCUMENTS

| | | | |
|---|---|---|---|
| 9,623,443 B2 | 4/2017 | Yoshida et al. | |
| 2013/0338507 A1* | 12/2013 | Onishi | A61B 8/4444 600/459 |
| 2014/0070668 A1* | 3/2014 | Ona | B06B 1/0629 310/334 |
| 2014/0103781 A1 | 4/2014 | Nakamura et al. | |
| 2015/0231883 A1 | 8/2015 | Hirai et al. | |
| 2015/0258573 A1* | 9/2015 | Kojima | B06B 1/0622 310/327 |
| 2015/0266058 A1 | 9/2015 | Yoshida et al. | |
| 2016/0058417 A1* | 3/2016 | Kiyose | G01S 7/52079 600/472 |
| 2016/0329482 A1 | 11/2016 | Nakamura et al. | |
| 2017/0119346 A1* | 5/2017 | Atsuchi | A61B 8/4427 |
| 2017/0263846 A1* | 9/2017 | Nakamura | A61B 8/4427 |
| 2017/0285153 A1* | 10/2017 | Sato | G01S 15/8927 |
| 2018/0132827 A1* | 5/2018 | Nakanishi | G01S 15/8915 |
| 2018/0192995 A1* | 7/2018 | Osawa | A61B 8/15 |
| 2018/0257927 A1* | 9/2018 | Rothberg | H01L 41/22 |

FOREIGN PATENT DOCUMENTS

| | | |
|---|---|---|
| JP | 2015-171809 A | 10/2015 |
| JP | 2015-185915 A | 10/2015 |
| JP | 2015-188208 A | 10/2015 |

* cited by examiner

ULTRASONIC DEVICE AND ULTRASONIC APPARATUS

BACKGROUND

1. Technical Field

The present invention relates to an ultrasonic device and an ultrasonic apparatus.

2. Related Art

In the related art, an ultrasonic sensor (ultrasonic device) including a substrate in which an opening is formed, a vibrating plate provided on the substrate so as to close the opening, a piezoelectric element provided on the vibrating plate on the side opposite to the opening, and a sealing plate sealing the periphery of the piezoelectric element has been known (e.g., see JP-A-2015-188208).

The ultrasonic device disclosed in JP-A-2015-188208 performs the transmission and reception of ultrasonic waves in the state where the ultrasonic device is in contact with an object of measurement. That is, the ultrasonic device drives the piezoelectric element to vibrate the vibrating plate and thus transmits ultrasonic waves through the opening. Moreover, the ultrasonic device detects an electric signal that is output from the piezoelectric element in response to the vibration of the vibrating plate due to ultrasonic waves incident thereon, and thus receives the ultrasonic waves.

In the ultrasonic device disclosed in JP-A-2015-188208, by sealing the periphery of the piezoelectric element, that is, an internal space in which the piezoelectric element is accommodated, with the sealing plate as described above, the inflow of a foreign substance such as moisture or dust from the external space into the internal space can be suppressed, and thus the deterioration of the piezoelectric element and the like, that is, the performance degradation of the ultrasonic sensor, due to the foreign substance can be suppressed.

In the ultrasonic device described above, however, when a pressure difference occurs between the internal and external spaces present with the vibrating plate therebetween, the vibrating plate or the piezoelectric element may be broken or deteriorated. For example, when the substrate side of the ultrasonic device is strongly brought into contact with the object of measurement, a stress from the sealing plate side toward the substrate side acts on the vibrating plate or the piezoelectric element because an internal pressure in the internal space is increased. Also, when, for example, an abrupt pressure difference occurs between the internal space and the external space in reducing a pressure in the external space during manufacture, the stress in the direction from the sealing plate toward the substrate acts on the vibrating plate or the piezoelectric element. The vibrating plate or the piezoelectric element is broken or deteriorated due to the stress described above, so that the performance of the ultrasonic device may be degraded.

SUMMARY

An advantage of some aspects of the invention is to provide an ultrasonic device and an ultrasonic apparatus whose performance degradation can be suppressed.

An ultrasonic device according to an application example of the invention includes: a substrate including a first groove portion and a second groove portion in a first surface; a vibration film provided on the first surface and closing the first groove portion and the second groove portion; a first piezoelectric element provided on the vibration film and overlapping the first groove portion in a plan view as viewed in a thickness direction of the substrate; and a second piezoelectric element provided on the vibration film and overlapping the second groove portion in the plan view, wherein the substrate is provided with a third groove portion coupling the first groove portion to the second groove portion, the substrate is provided with a fourth groove portion extending in a direction away from the first piezoelectric element and the second piezoelectric element in the plan view and coupled to the third groove portion, and a hole portion coupling a second surface of the substrate that is opposed to the first surface to the fourth groove portion is provided.

In the application example, the first groove portion and the second groove portion provided in the first surface of the substrate are closed by the vibration film on the first surface side, and thus an internal space is formed. The first groove portion and the second groove portion are coupled through the third groove portion. The third groove portion is coupled to the fourth groove portion, and the fourth groove portion is coupled to the hole portion opened in the second surface opposed to the first surface. That is, the internal space communicates with an external space through the third groove portion and the fourth groove portion. With this configuration, the occurrence of the pressure difference between the internal space and the external space described above can be suppressed, and thus the breakage or deterioration of the piezoelectric element or the vibration film due to the pressure difference can be suppressed.

Moreover, the fourth groove portion is extended in the direction away from the first piezoelectric element and the second piezoelectric element in the plan view, is coupled at the other end, relative to one end communicating with the third groove portion, to the hole portion in the second surface, and communicates with the outside. In such a configuration, the length dimension of the fourth groove portion can be increased irrespective of the thickness dimension of the substrate, and thus the inflow of a foreign substance from the external space into the internal space can be suppressed.

Moreover, since the fourth groove portion communicates with the first groove portion and the second groove portion, that is, with the internal space through the third groove portion, the inflow of a foreign substance into the internal space can be more reliably suppressed compared to the case where the fourth groove portion directly communicates with the internal space.

From the above, the performance degradation of the ultrasonic device can be suppressed, and thus reliability can be improved.

In the ultrasonic device of the application example, it is preferable that the cross-sectional area of the fourth groove portion is smaller than the cross-sectional area of the third groove portion.

Here, the cross-sectional area of the fourth groove portion is a cross-sectional area in a plane crossing the extending direction of the fourth groove portion. Similarly, the cross-sectional area of the third groove portion is a cross-sectional area in a plane crossing the extending direction of the third groove portion.

In the application example with the configuration described above, by making the cross-sectional area of the fourth groove portion smaller than the cross-sectional area of the third groove portion, a flow path resistance of the fourth groove portion can be increased, and thus the inflow of a foreign substance from the external space can be more effectively suppressed.

In the ultrasonic device of the application example, it is preferable that an inner surface of the fourth groove portion includes a plurality of depressions and projections.

In the application example with this configuration, the flow path resistance of the fourth groove portion can be increased by forming the plurality of depressions and projections on the inner surface of the fourth groove portion, and thus the inflow of a foreign substance from the external space can be more effectively suppressed.

In the ultrasonic device of the application example, it is preferable that an inner surface of the third groove portion includes a plurality of depressions and projections.

In the application example with this configuration, a flow path resistance of the third groove portion can be increased by forming the plurality of depressions and projections on the inner surface forming the third groove portion. Hence, the inflow of a foreign substance from the external space into the first groove portion and the second groove portion through the third groove portion can be suppressed.

In the ultrasonic device of the application example, it is preferable that the fourth groove portion is further extended along an outer periphery of the substrate.

In the application example with this configuration, the fourth groove portion is extended to the vicinity of the outer periphery of the substrate in the plan view, and further extended along the outer periphery. With this configuration, the length dimension of the fourth groove portion can be further increased, and thus the inflow of a foreign substance from the external space into the internal space can be more reliably suppressed.

In the ultrasonic device of the application example, it is preferable that the fourth groove portion includes a meandering portion meandering in the plan view.

In the application example with this configuration, since the fourth groove portion includes the meandering portion, the fourth groove portion can be lengthened compared to the case where the meandering portion is absent. Moreover, since the meandering portion includes a curved or bent portion, the flow path resistance can be increased at the curved position or the bent position, and thus the inflow of a foreign substance from the external space can be more effectively suppressed.

An ultrasonic device according to an application example of the invention includes: a substrate including a first groove portion and a second groove portion in a first surface; a vibration film provided on the first surface and closing the first groove portion and the second groove portion; a first piezoelectric element provided on the vibration film and overlapping the first groove portion in a plan view as viewed in a thickness direction of the substrate; and a second piezoelectric element provided on the vibration film and overlapping the second groove portion in the plan view, wherein the first groove portion and the second groove portion extend in a first direction and are adjacent to each other in a second direction crossing the first direction, the substrate is provided with a third groove portion extending in the second direction and coupling one end side of the first groove portion to one end side of the second groove portion, the substrate is provided with a fourth groove portion extending in a direction away from the first piezoelectric element and the second piezoelectric element in the plan view and coupled at one end side to the third groove portion, and a hole portion coupling a second surface of the substrate that is opposed to the first surface to the other end side of the fourth groove portion is provided.

In the application example, the one end side of the first groove portion and the one end side of the second groove portion are coupled to the third groove portion. The one end side of the fourth groove portion is coupled to the third groove portion, and the other end side is coupled to the hole portion opened in the second surface opposed to the first surface. In the application example, since the internal space communicates with the external space through the third groove portion and the fourth groove portion similarly to the application example relating to the ultrasonic device described above, the occurrence of the pressure difference between the internal space and the external space described above can be suppressed, and thus the breakage or deterioration of the piezoelectric element or the vibration film due to the pressure difference can be suppressed.

Moreover, the fourth groove portion is extended in the direction away from the first piezoelectric element and the second piezoelectric element in the plan view, is coupled at the other end, relative to one end communicating with the third groove portion, to the hole portion opened in the second surface, and communicates with the outside. In such a configuration, the length dimension of the fourth groove portion can be increased irrespective of the thickness dimension of the substrate, and thus the inflow of a foreign substance from the external space into the internal space can be suppressed.

Moreover, since the fourth groove portion communicates with the first groove portion and the second groove portion, that is, with the internal space through the third groove portion, the inflow of a foreign substance into the internal space can be more reliably suppressed compared to the case where the fourth groove portion directly communicates with the internal space.

From the above, the performance degradation of the ultrasonic device can be suppressed, and thus reliability can be improved.

An ultrasonic apparatus according to an application example of the invention includes: a substrate including a first groove portion and a second groove portion in a first surface; a vibration film provided on the first surface and closing the first groove portion and the second groove portion; a first piezoelectric element provided on the vibration film and overlapping the first groove portion in a plan view as viewed in a thickness direction of the substrate; a second piezoelectric element provided on the vibration film and overlapping the second groove portion in the plan view; and a control unit controlling the first piezoelectric element and the second piezoelectric element, wherein the substrate is provided with a third groove portion coupling the first groove portion to the second groove portion, the substrate is provided with a fourth groove portion extending in a direction away from the first piezoelectric element and the second piezoelectric element in the plan view and coupled to the third groove portion, and a hole portion coupling a second surface of the substrate that is opposed to the first surface to the fourth groove portion is provided.

In the application example, since the internal space communicates with the external space through the third groove portion and the fourth groove portion similarly to the application example relating to the ultrasonic device described above, the occurrence of the pressure difference between the internal space and the external space described above can be suppressed, and thus the breakage or deterioration of the piezoelectric element or the vibration film due to the pressure difference can be suppressed.

Moreover, the fourth groove portion is extended in the direction away from the first piezoelectric element and the second piezoelectric element in the plan view, is coupled at the other end, relative to one end communicating with the third groove portion, to the hole portion opened in the second surface, and communicates with the outside. In such a configuration, the length dimension of the fourth groove portion can be increased irrespective of the thickness dimension of the substrate, and thus the inflow of a foreign substance from the external space into the internal space can be suppressed.

Moreover, since the fourth groove portion communicates with the first groove portion and the second groove portion, that is, with the internal space through the third groove portion, the inflow of a foreign substance into the internal space can be more reliably suppressed compared to the case where the fourth groove portion directly communicates with the internal space.

From the above, the performance degradation of the ultrasonic apparatus can be suppressed, and thus reliability can be improved.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

Hereinafter, a first embodiment will be described based on the drawings.

Figure 1:
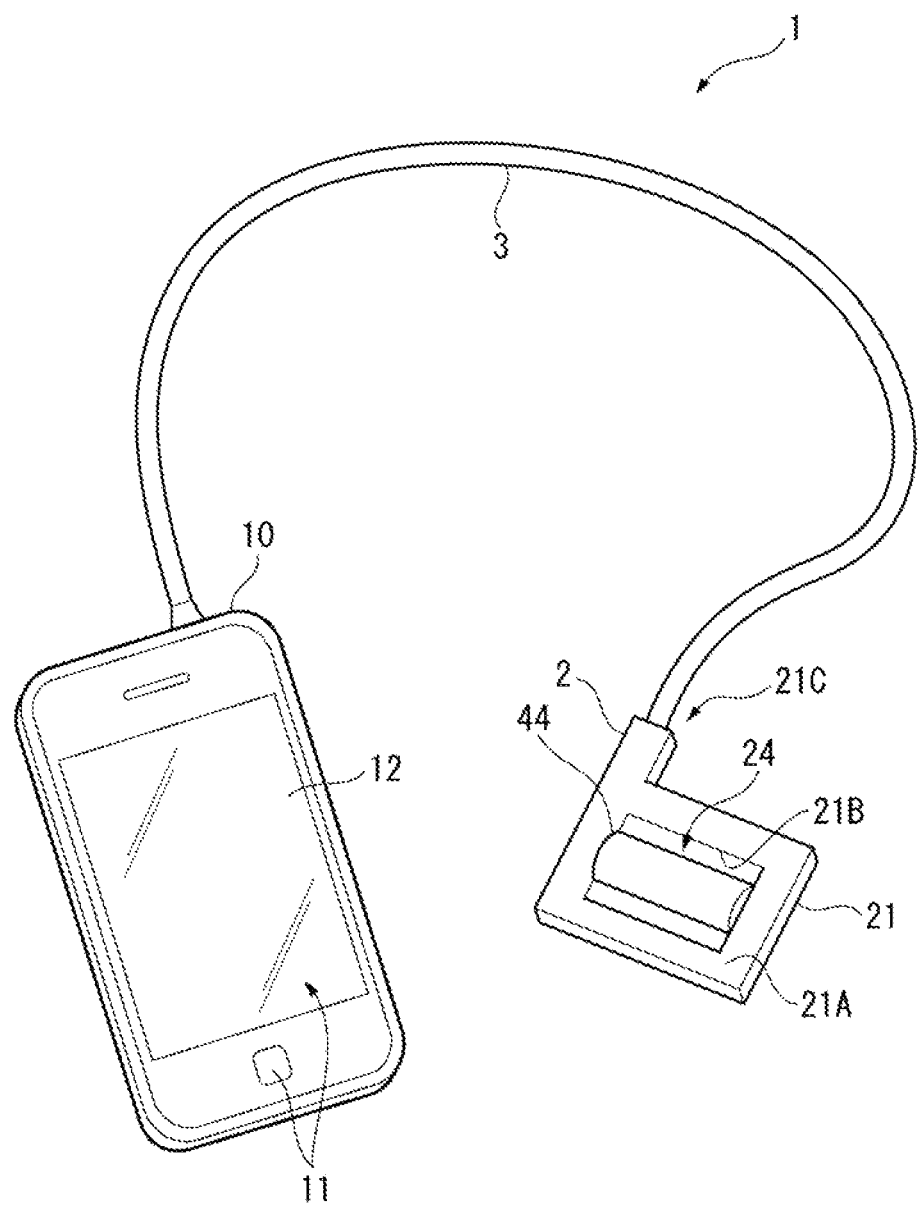
FIG. 1 is a diagram showing a schematic configuration of an ultrasonic apparatus of a first embodiment.

FIG. 1 is a perspective view showing a schematic configuration of an ultrasonic measurement apparatus 1.

The ultrasonic measurement apparatus 1 corresponds to an ultrasonic apparatus, and includes an ultrasonic probe 2 and a controller 10 electrically connected to the ultrasonic probe 2 through a cable 3 as shown in FIG. 1.

The ultrasonic measurement apparatus 1 sends ultrasonic waves from the ultrasonic probe 2 into a living body (e.g., a human body) in the state where the ultrasonic probe 2 is in contact with the surface of the living body. The ultrasonic measurement apparatus 1 receives the ultrasonic waves reflected by an organ in the living body with the ultrasonic probe 2, and thus obtains, for example, an internal tomographic image in the living body or measures the condition of the organ in the living body (e.g., a blood flow, etc.) based on the received signal.

Configuration of Controller

The controller 10 corresponds to a control unit, and includes an operating unit 11 including a button and a touch panel, and a display unit 12 as shown in FIG. 1. Although not shown in the drawing, the controller 10 further includes a storage unit composed of a memory or the like, and a calculation unit composed of a central processing unit (CPU) or the like. The controller 10 causes the calculation unit to execute various programs stored in the storage unit to thereby control the ultrasonic measurement apparatus 1. For example, the controller 10 outputs an instruction to control driving of the ultrasonic probe 2, forms an image of an internal structure of the living body based on the received signal input from the ultrasonic probe 2 and causes the display unit 12 to display the image, or measures biological information such as a blood flow and causes the display unit 12 to display the biological information. As the controller 10, for example, a terminal device such as a tablet terminal, a smartphone, or a personal computer can be used, and a dedicated terminal device for operating the ultrasonic probe 2 may be used.

Configuration of Ultrasonic Probe

Figure 2:
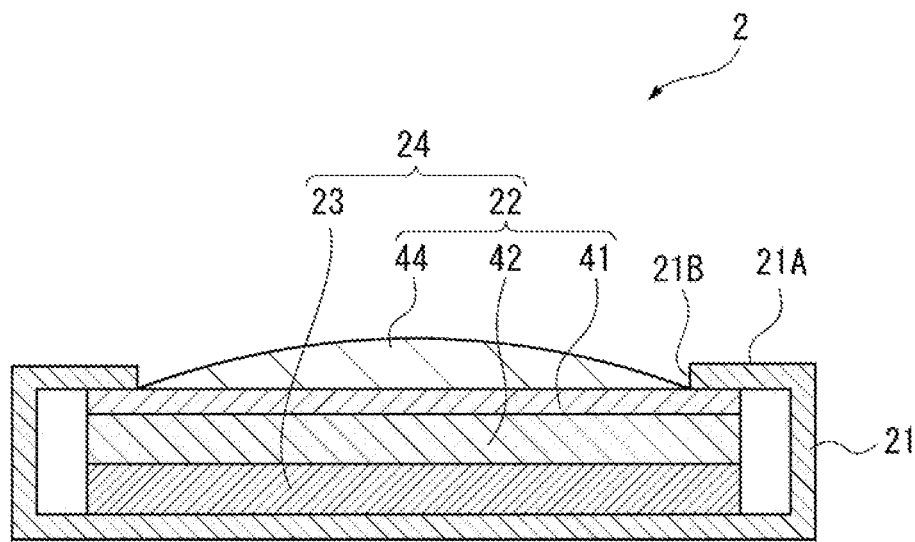
FIG. 2 is a cross-sectional view showing a schematic configuration of an ultrasonic probe of the first embodiment.

FIG. 2 is a cross-sectional view showing a schematic configuration of the ultrasonic probe 2.

As shown in FIG. 2, the ultrasonic probe 2 includes a housing 21, an ultrasonic device 22 accommodated inside the housing 21, and a circuit board 23 provided with a driver circuit and the like for controlling the ultrasonic device 22. The ultrasonic device 22 and the circuit board 23 constitute an ultrasonic sensor 24 corresponding to an ultrasonic module.

Configuration of Housing

As shown in FIG. 1, the housing 21 is formed in, for example, a rectangular box shape in a plan view. A sensor window 21B is provided in one surface (sensor surface 21A) orthogonal to the thickness direction, so that a portion of the ultrasonic device 22 is exposed. A passage hole 21C of the cable 3 is provided in a portion of the housing 21 (in a side surface thereof in the example shown in FIG. 1), and the cable 3 is connected to the circuit board 23 inside the housing 21 through the passage hole 21C. A gap between the cable 3 and the passage hole 21C is filled with, for example, a resin material, so that waterproofness is ensured.

In the embodiment, the configuration in which the ultrasonic probe 2 and the controller 10 are connected to each other using the cable 3 is exemplified; however, the invention is not limited to this. For example, the ultrasonic probe 2 and the controller 10 may be connected to each other by wireless communication, or various configurations of the controller 10 may be provided in the ultrasonic probe 2.

Configuration of Circuit Board

The circuit board 23 is electrically connected with signal terminals 414P and common terminals 416P (see FIG. 3) of the ultrasonic device 22, and controls the ultrasonic device 22 based on the control of the controller 10.

Specifically, the circuit board 23 includes a transmitting circuit and a receiving circuit. The transmitting circuit outputs a drive signal that causes the ultrasonic device 22 to transmit ultrasonic waves. The receiving circuit obtains a received signal output from the ultrasonic device 22 receiving ultrasonic waves. The receiving circuit performs amplification processing, A-D conversion processing, phasing addition processing, and the like on the received signal, and outputs the resultant to the controller 10.

Configuration of Ultrasonic Device

Figure 3:
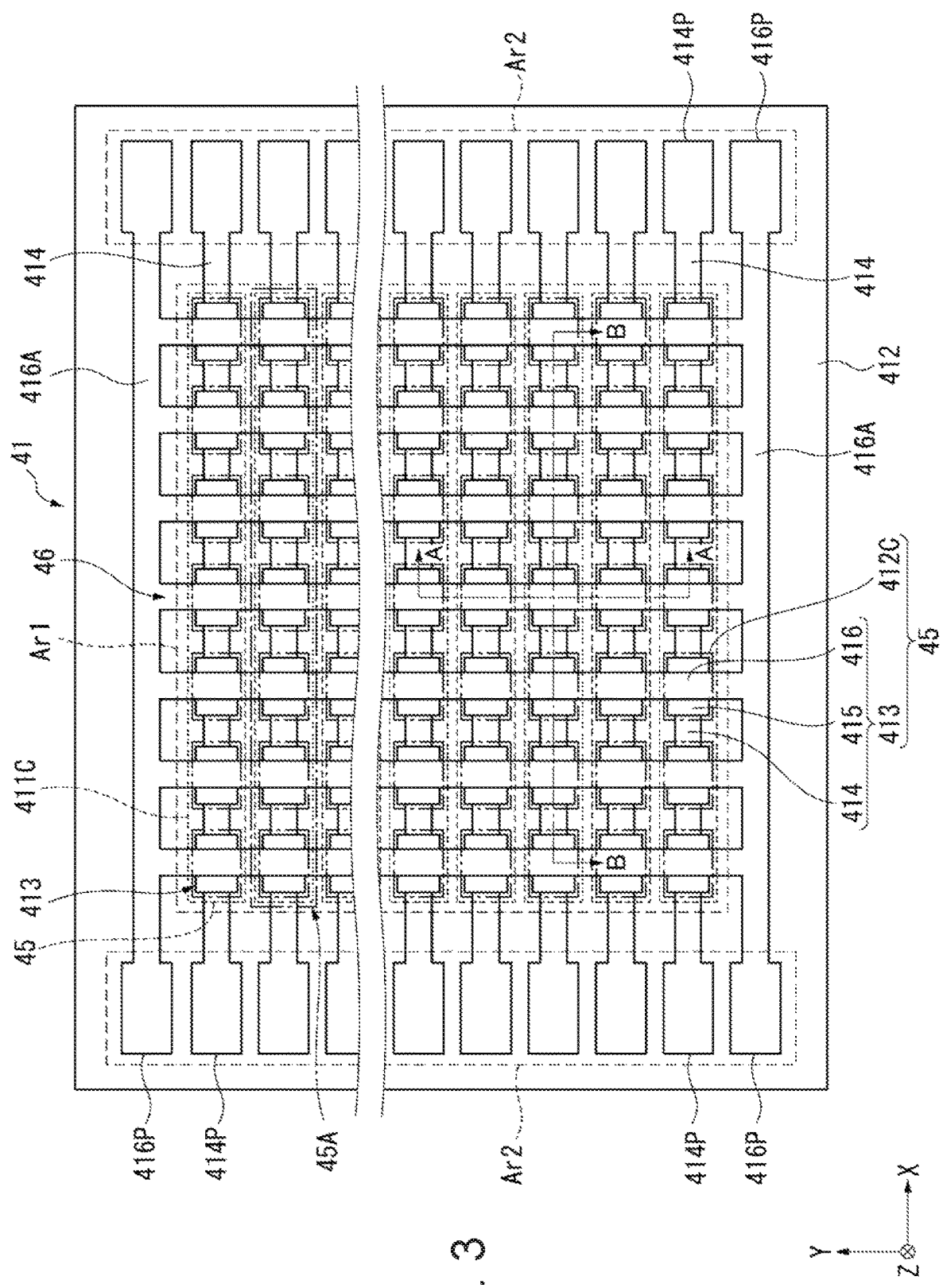
FIG. 3 is a plan view showing a schematic configuration of an element substrate of an ultrasonic device of the first embodiment.
Figure 4:
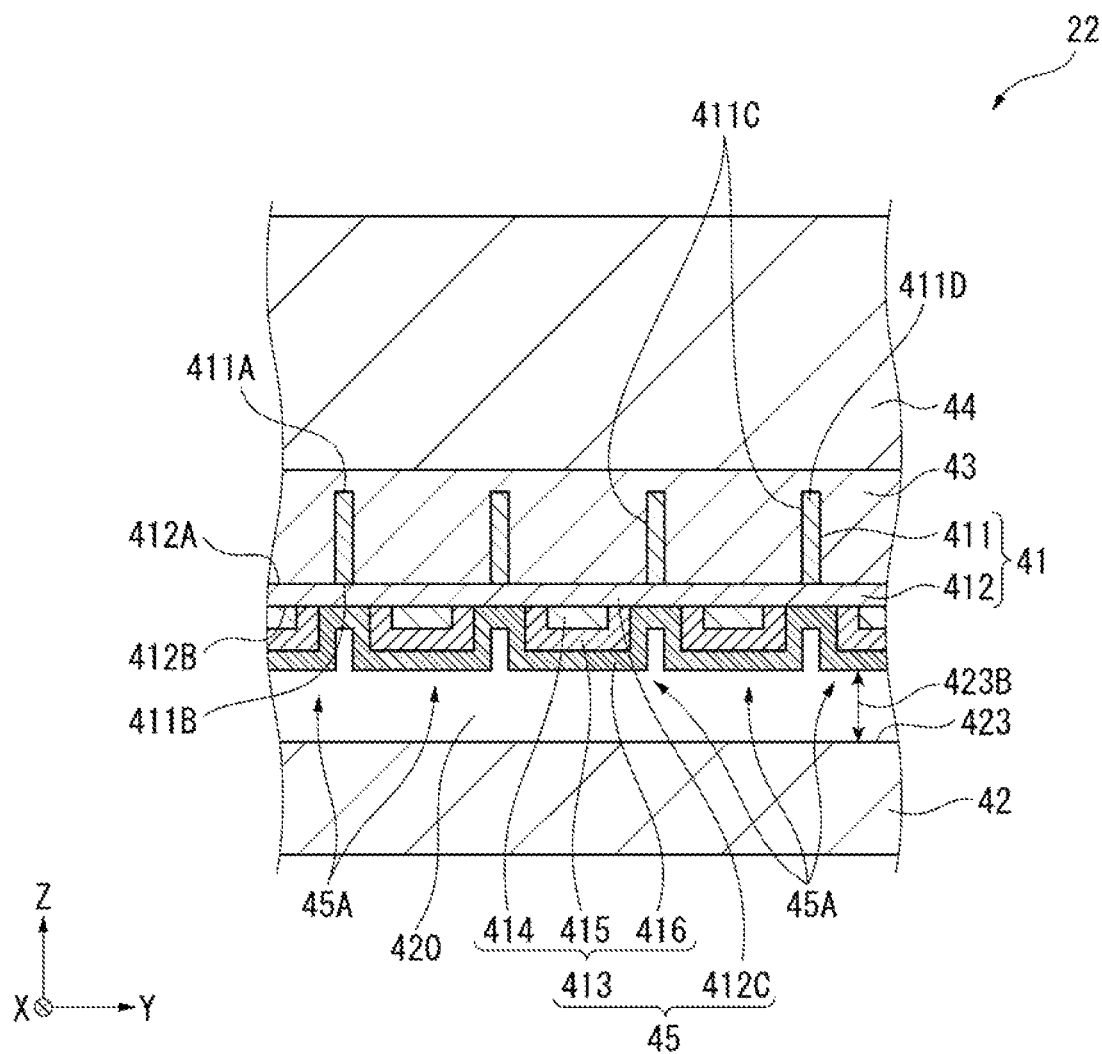
FIG. 4 is a cross-sectional view schematically showing a cross-section of the ultrasonic device of the first embodiment.
Figure 5:
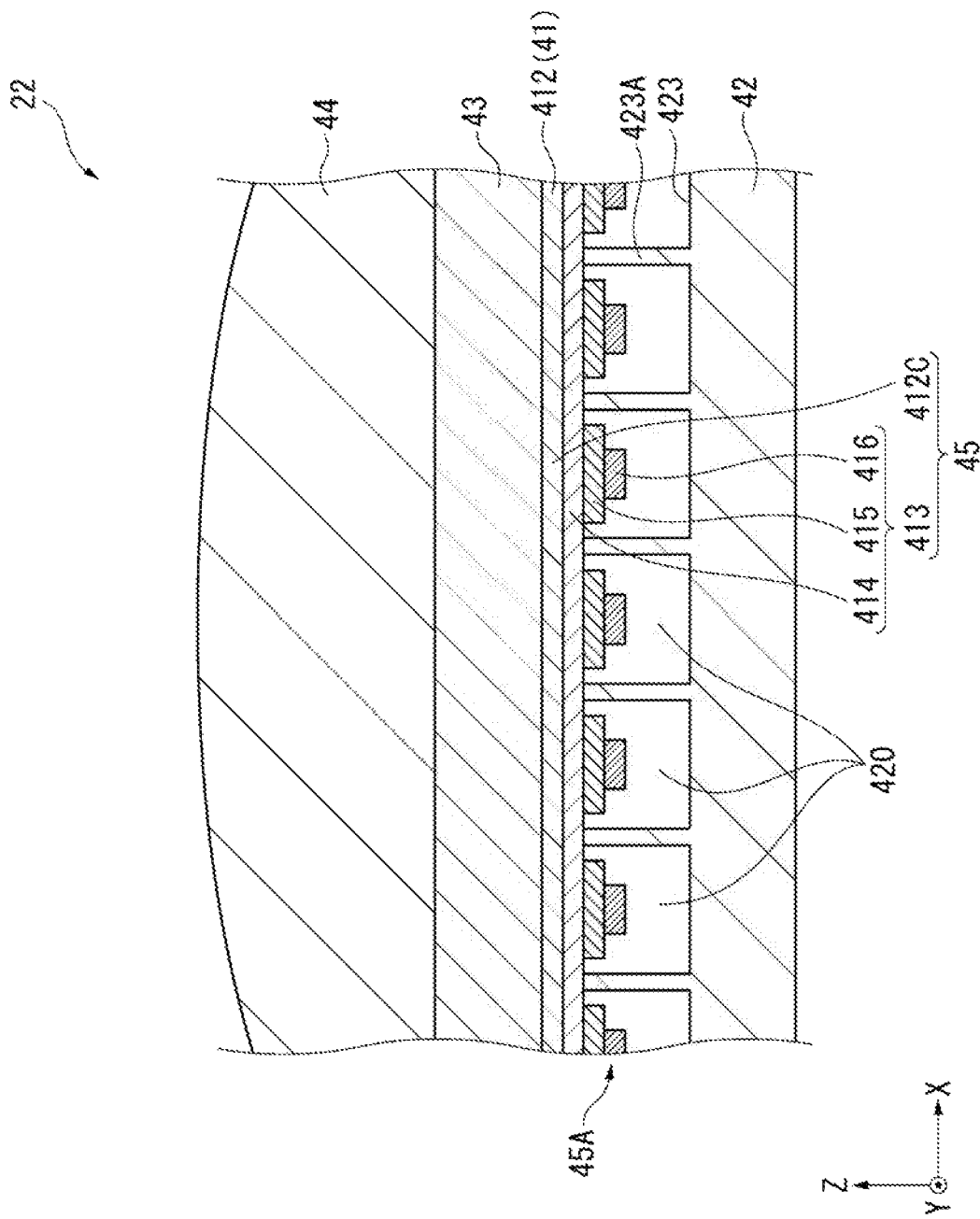
FIG. 5 is a cross-sectional view schematically showing a cross-section of the ultrasonic device of the first embodiment.
Figure 6:
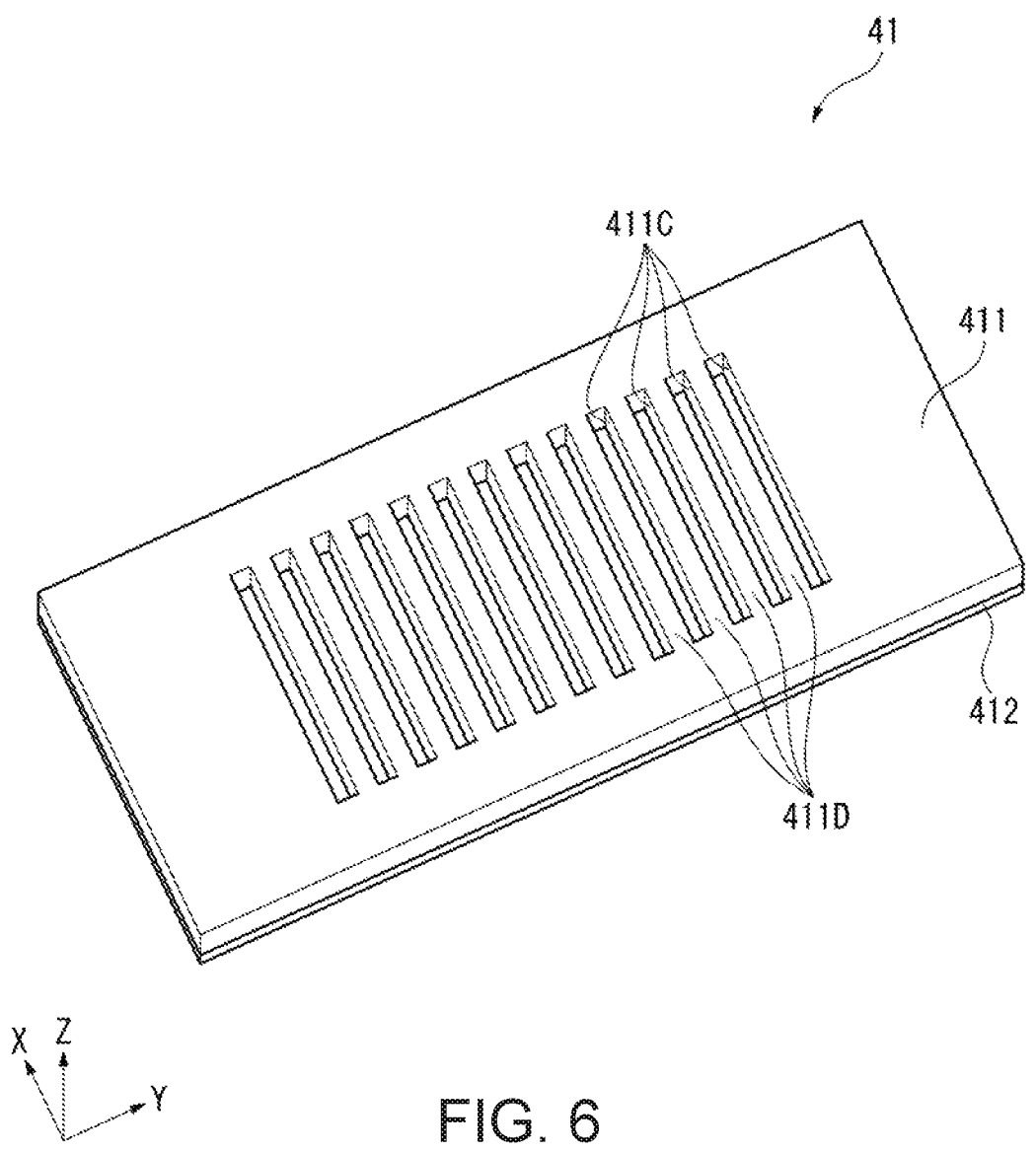
FIG. 6 is a perspective view showing a schematic configuration of the element substrate of the first embodiment.

FIG. 3 is a plan view of an element substrate 41 in the ultrasonic device 22 as viewed from a sealing plate 42 side. FIG. 4 is a cross-sectional view of the ultrasonic device 22 taken along line A-A in FIG. 3. FIG. 5 is a cross-sectional view of the ultrasonic device 22 taken along line B-B in FIG. 3. FIG. 6 is a perspective view showing a schematic configuration of the element substrate 41 as viewed from an acoustic lens 44 side.

As shown in FIGS. 4 and 5, the ultrasonic device 22 is composed of the element substrate 41, the sealing plate 42, an acoustic layer 43, and the acoustic lens 44.

Configuration of Element Substrate

As shown in FIG. 4, the element substrate 41 includes a substrate main body 411, a vibration film 412 provided on the sealing plate 42 side of the substrate main body 411, and piezoelectric elements 413 provided on the vibration film 412.

In the following description, a surface of the substrate main body 411 on the acoustic lens 44 side is referred to as a "front surface 411A", while a surface facing the sealing plate 42 is referred to as a "rear surface 411B". A surface of the vibration film 412 on the side opposite to the sealing plate 42 is referred to as an "opening surface 412A", while a surface on the sealing plate 42 side is referred to as a "working surface 412B".

As shown in FIG. 3, the element substrate 41 is provided with an ultrasonic transducer array (transducer array) 46 as a one-dimensional array including a plurality of ultrasonic transducers 45 disposed in an array. That is, in a plan view when the element substrate 41 is viewed in the substrate thickness direction (Z-direction) (hereinafter also simply referred to as a "plan view"), the plurality of ultrasonic transducers 45 are disposed in a matrix and constitute the ultrasonic transducer array 46 in an array region Ar1 in the center of the element substrate 41. The ultrasonic transducer array 46 includes a plurality of transmission and reception columns 45A each composed of the plurality of ultrasonic transducers 45 that are disposed along the X-direction (slice direction), and each functioning as a transmission and reception channel of 1CH. The plurality of transmission and reception columns 45A are disposed in the Y-direction (scanning direction). In FIG. 3, the number of disposed ultrasonic transducers 45 is reduced for convenience of description; actually, however, a larger number of ultrasonic transducers 45 are disposed.

The substrate main body 411 is a substrate that supports the vibration film 412, and is composed of, for example, a semiconductor substrate of Si or the like. As shown in FIG. 4, the substrate main body 411 is provided with openings 411C overlapping the transmission and reception columns 45A in the plan view. As shown in FIG. 6, the opening 411C is formed along the X-direction. As shown in FIG. 4, the opening 411C overlaps the transmission and reception column 45A in the plan view, and defines the dimension of the ultrasonic transducer 45 in the Y-direction.

The vibration film 412 is composed of, for example, $SiO_2$ or a stacked body of $SiO_2$ and $ZrO_2$, and is provided on the rear surface 411B of the substrate main body 411. That is, as shown in FIG. 4, the vibration film 412 is supported by wall portions 411D constituting the openings 411C, and closes the rear surface 411B side of the openings 411C. The thickness dimension of the vibration film 412 is sufficiently small relative to the substrate main body 411.

Although described in detail later, groove portions 423 that are disposed along the Y-direction so as to cross the openings 411C in the plan view and respectively correspond to the plurality of ultrasonic transducers 45 disposed in the X-direction are formed in the sealing plate 42 as shown in FIG. 5. The dimension of the ultrasonic transducer 45 in the X-direction is defined by the groove portion 423. That is, the vibration film 412 closes the openings 411C and the groove portions 423 (see FIGS. 4 and 5). A region of the vibration film 412 that is surrounded by the opening 411C and the groove portion 423 in the plan view is a vibration region, which is hereinafter referred to as a "flexible portion 412C". The flexible portion 412C is provided at a position corresponding to each of the ultrasonic transducers 45. The dimension of the flexible portion 412C in the X-direction is defined by the groove portion 423 as shown in FIG. 5, while the dimension in the Y-direction is defined by the openings 411C as shown in FIG. 4.

The piezoelectric element 413, which is a stacked body of a lower electrode 414, a piezoelectric film 415, and an upper electrode 416, is provided on the working surface 412B of the flexible portion 412C. The flexible portion 412C and the piezoelectric element 413 constitute one ultrasonic transducer 45.

In the ultrasonic transducer 45, a pulse wave voltage at a predetermined frequency is applied between the lower electrode 414 and the upper electrode 416 to vibrate the flexible portion 412C in the opening region of the opening 411C, so that ultrasonic waves are transmitted from the opening surface 412A side. When the flexible portion 412C is vibrated by ultrasonic waves that are reflected from an object and incident on the opening surface 412A, a potential difference occurs between the upper and lower sides of the piezoelectric film 415. Hence, the ultrasonic waves are detected, that is, received by detecting the potential difference occurring between the lower electrode 414 and the upper electrode 416.

As shown in FIG. 3, the lower electrode 414 is linearly formed along the X-direction and constitutes the transmission and reception column 45A of 1CH. The signal terminals 414P electrically connected to the circuit board 23 are provided in a terminal region Ar2 at both ends (±X-side ends) of the lower electrode 414.

As shown in FIG. 3, the upper electrode 416 is linearly formed along the Y-direction and connects the transmission and reception columns 45A arranged in the Y-direction. The ±Y-side ends of the upper electrode 416 are connected to common electrode lines 416A. The common electrode line 416A connects a plurality of the upper electrodes 416 disposed along the X-direction to each other. The common terminals 416P electrically connected to the circuit board 23 are provided at both ends (±X-side ends) of the common electrode line 416A. The common terminals 416P are connected to a reference potential circuit (not shown) of the circuit board 23, and set to a reference potential.

Configurations of Acoustic Layer and Acoustic Lens

As shown in FIGS. 4 and 5, the acoustic layer 43 is provided on the surface (the front surface 411A of the substrate main body 411 and the opening surface 412A of the vibration film 412) of the element substrate 41 on the +Z-side.

As shown in FIG. 1, the acoustic lens 44 is exposed to the outside through the sensor window 21B of the housing 21, and is brought into contact with the surface of a living body as an object of measurement. The acoustic lens 44 has a cylindrical shape in cross-section in the ZX plane (see FIG. 5), and converges ultrasonic waves transmitted from the ultrasonic device 22.

The acoustic layer 43 and the acoustic lens 44 are formed of a viscoelastic body or an elastomer, and can be formed using, for example, a silicone rubber or a butadiene rubber. The acoustic layer 43 and the acoustic lens 44 have an acoustic impedance (e.g., 1.5 MRayls) close to the acoustic impedance of the living body as an object of measurement. With this configuration, the acoustic layer 43 and the acoustic lens 44 efficiently propagate ultrasonic waves transmitted from the ultrasonic transducer 45 to the living body as an object of measurement, and efficiently propagate the ultrasonic waves reflected in the living body to the ultrasonic transducer 45.

Configuration of Sealing Plate

Figure 7:
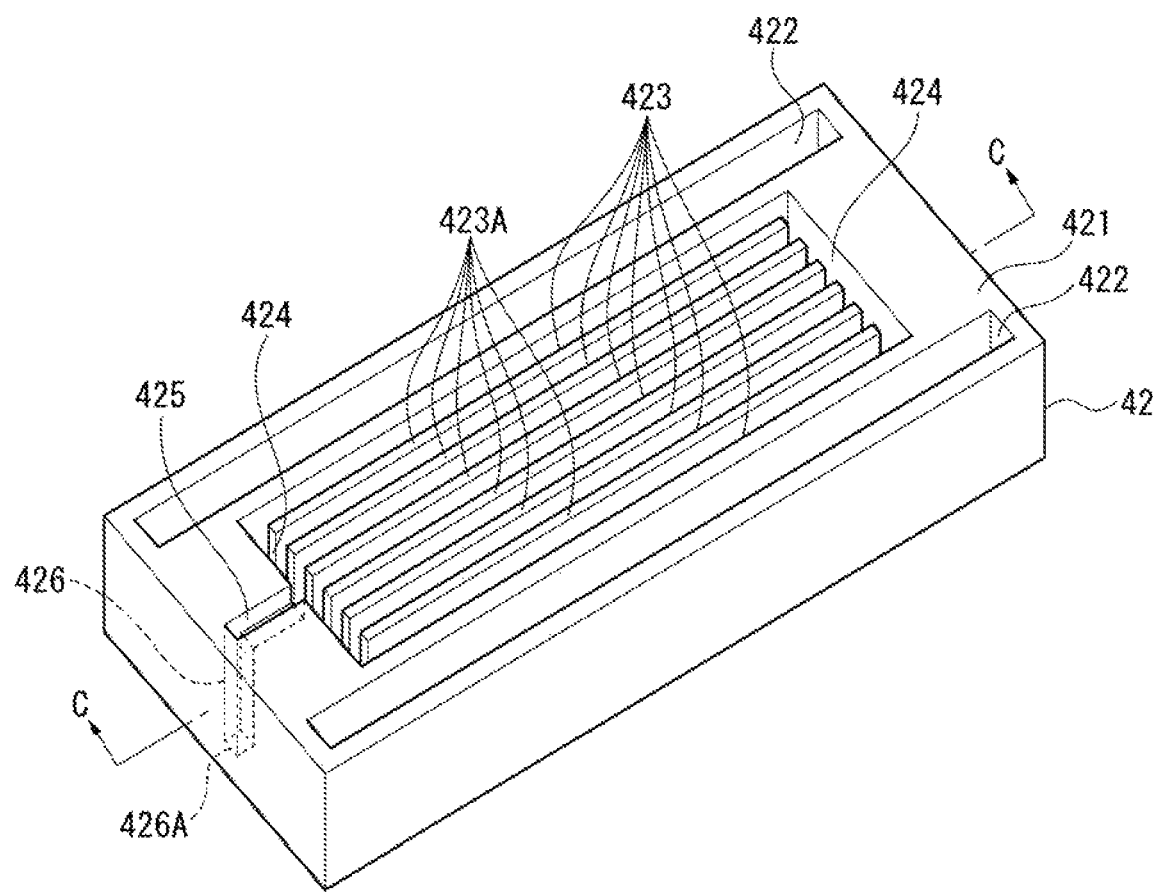
FIG. 7 is a perspective view showing a schematic configuration of a sealing plate of the first embodiment.
Figure 8:
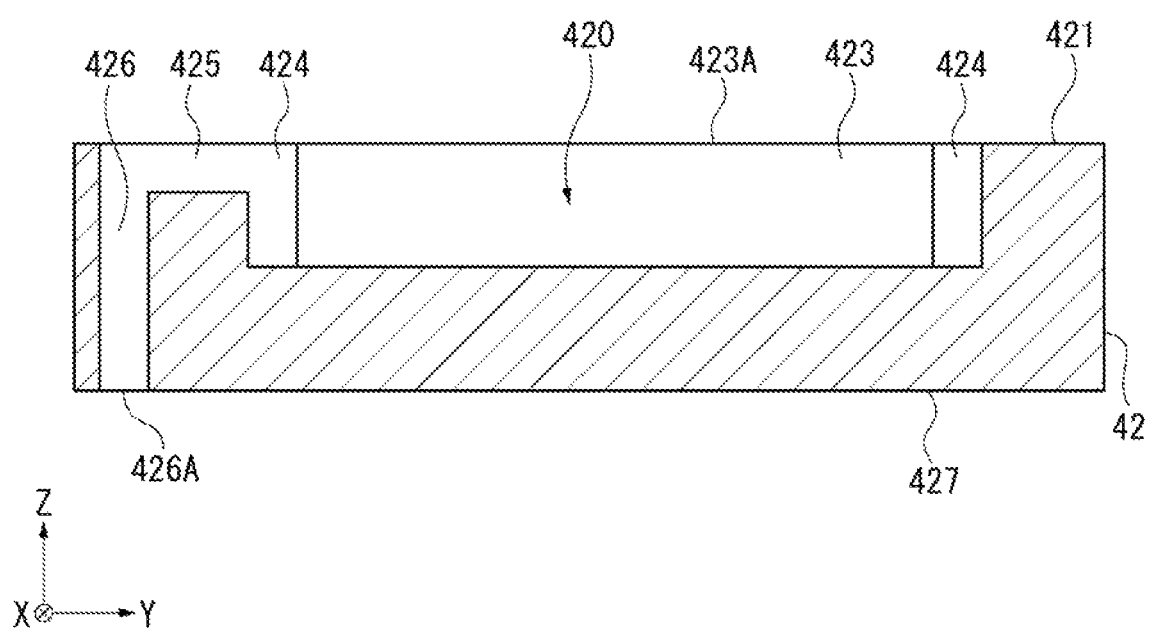
FIG. 8 is a cross-sectional view showing a schematic configuration of the sealing plate of the first embodiment.

FIG. 7 is a perspective view showing a schematic configuration of the sealing plate 42 as viewed from the element substrate 41 side. FIG. 8 is a cross-sectional view of the sealing plate 42 taken along line C-C in FIG. 7.

The sealing plate 42 corresponds to a substrate. The planar shape thereof as viewed in the thickness direction is formed in the same shape as, for example, the element substrate 41. A surface 421 (hereinafter also referred to as a "bonding surface 421") of the sealing plate 42 on the +Z-side corresponds to a first surface, and is bonded to the surface (the working surface 412B of the vibration film 412) of the element substrate 41 on the −Z-side with an adhesive or the like (not shown). The sealing plate 42 is composed of a semiconductor substrate of Si or the like, or an insulator substrate. The material and thickness of the sealing plate 42 affect the frequency characteristics of the ultrasonic transducer 45, and therefore, it is preferable to set the material and thickness based on the center frequency of ultrasonic waves transmitted and received by the ultrasonic transducer 45.

As shown in FIG. 7, wiring portions 422, the groove portions 423, coupling paths 424, a communication path 425, and a hole portion 426 are formed in the sealing plate 42.

The wiring portions 422 are provided in positions facing the terminal region Ar2 of the element substrate 41, and are through-holes penetrating the sealing plate 42 in the Z-direction. The terminals 414P and 416P are disposed at positions overlapping the wiring portions 422 as viewed from the −Z-side, and are connected to the circuit board 23 through wiring members (not shown), such as a flexible printed circuit (FPC), a cable line, and a wire, disposed in the wiring portions 422.

The groove portions 423 correspond to a first groove portion, a second groove portion, and a groove portion. The plurality of groove portions 423 are formed in a region facing the array region Ar1 of the element substrate 41. The groove portion 423 is a recessed groove opened in the bonding surface 421, and is closed by the vibration film 412 to form a vibration space of the piezoelectric element 413 of the ultrasonic transducer 45.

Specifically, the groove portion 423 is formed so as to extend in the Y-direction. The groove portions 423 are formed in positions respectively corresponding to the plurality of ultrasonic transducers 45 disposed in the X-direction. The groove portions 423 adjacent to each other in the X-direction crossing the Y-direction are separated from each other by a plurality of wall portions 423A formed along the Y-direction. In other words, in the plan view, the groove portion 423 crosses the transmission and reception column 45A along the X-direction and is formed in a position overlapping the ultrasonic transducers 45 constituting the transmission and reception column 45A (see FIG. 5). That is, the piezoelectric elements 413 (a first piezoelectric element and a second piezoelectric element) are provided at positions overlapping the groove portion 423.

The wall portions 423A adjacent to each other in the X-direction define the dimension of the flexible portion 412C in the X-direction. That is, the dimension of the groove portion 423 in the X-direction (the distance between the wall portions 423A adjacent to each other in the X-direction) corresponds to the dimension of the ultrasonic transducer 45 in the X-direction (the dimension of the flexible portion 412C in the X-direction). The dimension of the groove portion 423 in the Y-direction is larger than the dimension of the transmission and reception column 45A in the Y-direction. The dimension of the groove portion 423 in the Z-direction is set to a dimension such that the vibrations of at least the flexible portion 412C and the piezoelectric element 413 are not hindered.

The coupling path 424 corresponds to a third groove portion. The coupling path 424 is a recessed groove formed on each of the ±Y-sides of the groove portions 423 so as to extend in the X-direction, and couples the plurality of groove portions 423. The coupling path 424 couples the ends of the plurality of groove portions 423 on the −Y-side. The coupling path 424 is opened in the bonding surface 421. As shown in FIG. 8, the dimension of the coupling path 424 in the Z-direction (the dimension in the thickness direction of the sealing plate 42, which is a depth dimension) is the same as that of the groove portion 423. Hence, when, for example, the groove portion 423 is formed by etching, the coupling path 424 can be simultaneously formed and thus the manufacturing process can be simplified.

The communication path 425 corresponds to a fourth groove portion. In the plan view, the communication path 425 is extended from the coupling path 424 in a direction away from the groove portion 423 overlapping the piezoelectric element 413, and communicates at an end on the side opposite to the coupling path 424 with the outside through the hole portion 426. In the embodiment, as shown in FIGS. 7 and 8, the communication path 425 is formed along the Y-direction and communicates at an end on the +Y-side with the coupling path 424 provided on the −Y-side of the groove portion 423. Moreover, the communication path 425 communicates at the end on the −Y-side with the hole portion 426 to thereby cause an internal space 420 (see FIG. 8) surrounded by the groove portions 423 and the vibration film 412 to communicate with the outside through the hole portion 426.

As shown in FIG. 8, the depth dimension (dimension in the Z-direction) of the communication path 425 is smaller than that of the groove portion 423 and the coupling path 424. The width dimension (dimension in the X-direction) of the communication path 425 is substantially the same as the width dimension (dimension in the Y-direction) of the coupling path 424. That is, the cross-sectional area of the communication path 425 in a plane (plane parallel to the ZX plane) crossing the extending direction thereof (Y-direction) is smaller than the cross-sectional area of the coupling path 424 in a plane (plane parallel to the YZ plane) crossing the extending direction thereof (X-direction).

The hole portion 426 is formed to penetrate the sealing plate 42 in the vicinity of the outer peripheral edge of the sealing plate 42 in the plan view. An end of the hole portion 426 on the +Z-side communicates with the communication path 425. An end of the hole portion 426 on the −Z-side is coupled to an opening 426A opened in a bottom surface 427 (corresponding to a second surface) of the sealing plate 42 on the −Z-side. That is, the communication path 425 is coupled through the hole portion 426 to the opening 426A opened in the bottom surface 427 opposed to the bonding surface 421.

Operations and Advantageous Effects of First Embodiment

In the first embodiment configured as described above, the following operations and advantageous effects can be obtained.

In the ultrasonic device 22, the occurrence of a pressure difference between the internal space 420 and the external space can be suppressed by causing the internal space 420 and the external space to communicate with each other through the coupling path 424 and the communication path 425.

For example, when the pressure in the external space is reduced at the time of manufacture of the ultrasonic device 22, the pressure in the internal space 420 becomes larger than that in the external space if the internal space is completely sealed, and thus an abrupt pressure difference may occur between the internal and external spaces. Moreover, for example, the ultrasonic probe 2 may be strongly brought into contact with an object of measurement at the time of ultrasonic wave measurement. In this case, the vibration film 412 is inwardly deformed by a stress acting from the element substrate 41 side of the ultrasonic device 22, the internal pressure in the internal space 420 is increased, and an abrupt pressure difference may occur similarly. When such a pressure difference occurs, a large stress acts on the vibration film 412 or the piezoelectric element 413. Therefore, the vibration film 412 or the piezoelectric element 413 may be broken or deteriorated to degrade the performance of the ultrasonic device 22.

In contrast, in the ultrasonic device 22, the plurality of groove portions 423 forming the internal space 420 are coupled by the coupling path 424, and the coupling path 424 communicates with the outside through the communication path 425 coupled to the hole portion 426. By causing the internal space 420 to communicate with the external space through the coupling path 424 and the communication path 425, the occurrence of a pressure difference between the internal space 420 and the external space can be suppressed, and thus the breakage or deterioration of the piezoelectric element 413 or the vibration film 412 due to the pressure difference can be suppressed.

Moreover, the communication path 425 is extended in the direction away from the piezoelectric element 413 in the plan view, is coupled at the end on the side opposite to the end communicating with the coupling path 424 to the hole portion 426, and thus communicates with the outside. In such a configuration, the length dimension of the communication path 425 can be increased irrespective of the thickness dimension of the sealing plate 42, and thus the inflow of a foreign substance into the internal space 420 can be suppressed.

Moreover, since the communication path 425 communicates with the plurality of groove portions 423, that is, with the internal space 420 through the coupling path 424, the inflow of a foreign substance into the internal space 420 can be more reliably suppressed compared to the case where the communication path 425 communicates with the internal space 420 without through the coupling path 424.

From the above, according to the embodiment, the performance degradation of the ultrasonic device 22 can be suppressed, and thus reliability can be improved.

The depth dimension of the communication path 425 is smaller than that of the coupling path 424, and the cross-sectional area of the communication path 425 is smaller than that of the coupling path 424. With this configuration, a flow path resistance of the communication path 425 can be increased more than that of the coupling path 424, and thus the inflow of a foreign substance from the external space can be more effectively suppressed.

Moreover, the communication path 425 is extended from the coupling path 424 along the XY plane, connected to the hole portion 426 formed along the Z-direction, and communicates with the external space in the opening 426A formed in the bottom surface 427 of the sealing plate 42. In such a configuration, a bent portion is formed in the flow path at a connection position of the communication path 425 and the hole portion 426, and a flow path resistance can be increased by the bent portion.

The coupling path 424 and the plurality of groove portions 423 are both grooves formed in the bonding surface 421, and have the same depth dimension. In such a configuration, the coupling path 424 and the plurality of groove portions 423 can be simultaneously formed, which eliminates the necessity of separately carrying out the process of forming, for example, the coupling path 424 and can simplify the manufacturing process.

Second Embodiment

Hereinafter, a second embodiment will be described.

In the first embodiment, the communication path 425 is linearly extended toward the hole portion 426 formed in the vicinity of the outer peripheral edge of the sealing plate 42 in the plan view, and communicates with the hole portion 426. In contrast, the second embodiment differs from the first embodiment in that the communication path is extended so as to go around the outer peripheral edge of the sealing plate in the plan view, and then communicates with the hole portion 426.

In the following description, configurations similar to those of the first embodiment are denoted by the same reference numerals and signs, and the description thereof is omitted or simplified.

Figure 9:
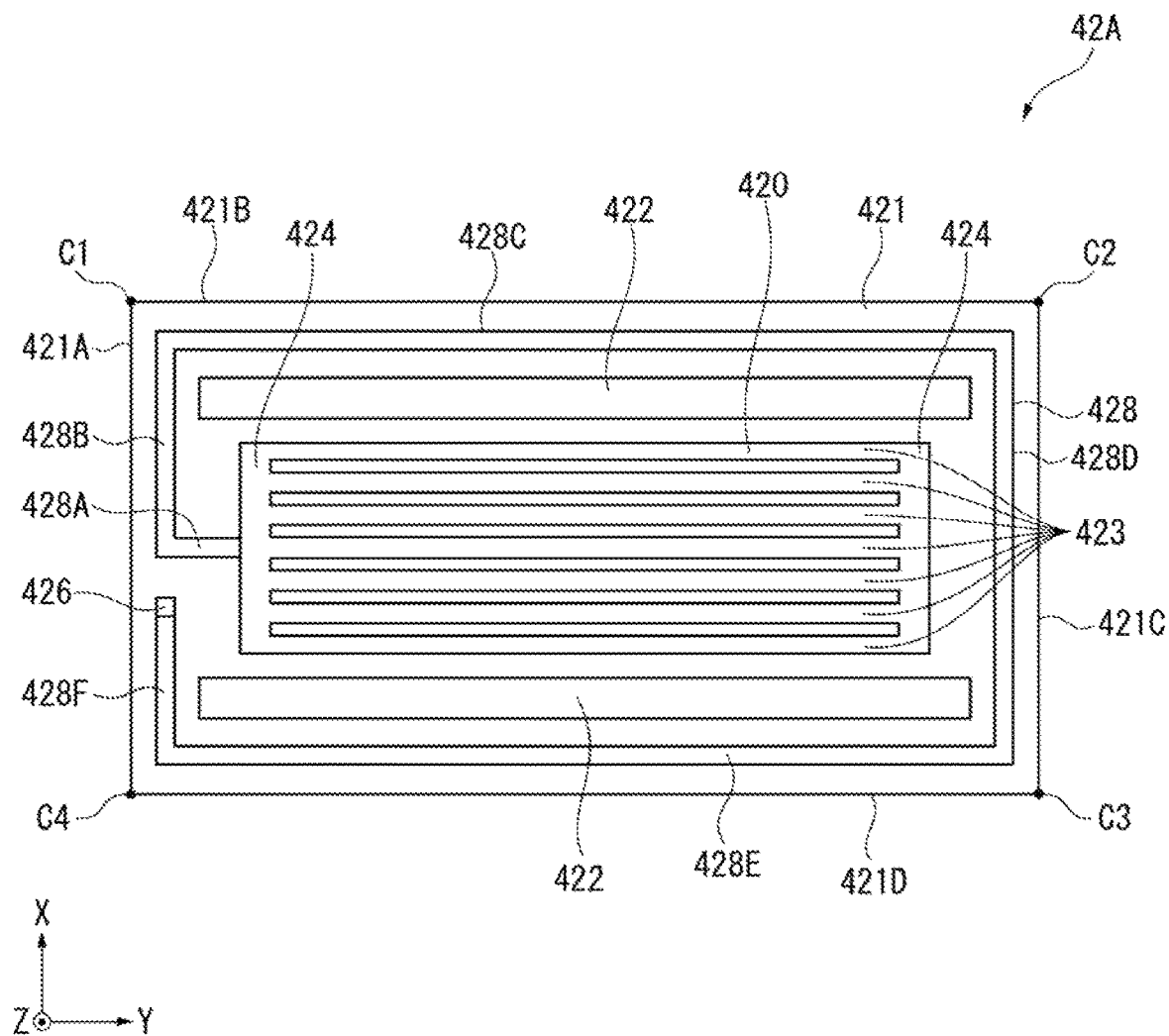
FIG. 9 is a plan view showing a schematic configuration of a sealing plate of a second embodiment.

FIG. 9 is a plan view schematically showing a sealing plate 42A as viewed from the element substrate 41 side.

In the four sides constituting the outer peripheral edge of the bonding surface 421 of the sealing plate 42A in the plan view, the side that is parallel to the X-direction and located on the −Y-side is defined as a first side 421A. The side that is parallel to the Y-direction and located on the +X-side is defined as a second side 421B. The side that is parallel to the X-direction and located on the +Y-side is defined as a third side 421C. The side that is parallel to the Y-direction and located on the −X-side is defined as a fourth side 421D.

Moreover, in the plan view, the point of intersection of the first side 421A and the second side 421B is defined as a point C1. The point of intersection of the second side 421B and the third side 421C is defined as a point C2. The point of intersection of the third side 421C and the fourth side 421D is defined as a point C3. The point of intersection of the fourth side 421D and the first side 421A is defined as a point C4.

A communication path 428 that communicates at one end with the coupling path 424 and communicates at the other end with the hole portion 426 is formed in the sealing plate 42A.

The communication path 428 includes a first communication portion 428A, a second communication portion 428B, a third communication portion 428C, a fourth communication portion 428D, a fifth communication portion 428E, and a sixth communication portion 428F. In the plan view, the first communication portion 428A is extended from the coupling path 424 in a direction away from the groove portion 423. The second communication portion 428B, the third communication portion 428C, the fourth communication portion 428D, the fifth communication portion 428E, and the sixth communication portion 428F are further extended from the first communication portion 428A along the outer peripheral edge of the sealing plate 42.

The first communication portion 428A is formed similarly to the communication path 425 of the first embodiment, except that the first communication portion 428A is not directly connected to the hole portion 426. In the plan view, the first communication portion 428A is extended in the Y-direction from the coupling path 424 toward the first side 421A of the sealing plate 42.

The second communication portion 428B is extended in the X-direction along the first side 421A from the first communication portion 428A to the vicinity of the point C1 in the plan view.

The third communication portion 428C is extended in the Y-direction along the second side 421B from the second communication portion 428B to the vicinity of the point C2 in the plan view.

The fourth communication portion 428D is extended in the X-direction along the third side 421C from the third communication portion 428C to the vicinity of the point C3 in the plan view.

The fifth communication portion 428E is extended in the Y-direction along the fourth side 421D from the fourth communication portion 428D to the vicinity of the point C4 in the plan view.

The sixth communication portion 428F is extended in the X-direction along the first side 421A from the fifth communication portion 428E to the hole portion 426 in the plan view.

Operations and Advantageous Effects of Second Embodiment

In the second embodiment configured as described above, the following operations and advantageous effects can be obtained in addition to the operations and advantageous effects of the first embodiment.

The communication path 428 is extended to the vicinity of the outer periphery of the sealing plate 42A in the plan view, and further extended along the outer periphery (the first side 421A, the second side 421B, the third side 421C, and the fourth side 421D). With this configuration, the path length of the communication path 428 can be further increased, and thus the inflow of a foreign substance from the external space into the internal space 420 can be more reliably suppressed.

In the embodiment, the communication path 428 is extended along the outer periphery of the sealing plate 42 so as to substantially go therearound. In such a configuration, the path length can be longer than that in the case where the communication path 428 is extended only along a portion of the outer periphery, for example, only along the two first and second sides 421A and 421B, or only along the three first, second, and third sides 421A, 421B, and 421C, and thus the inflow of a foreign substance can be more reliably suppressed.

Moreover, in the plan view, the communication path 428 is bent in the vicinities of the corners (the points C1 to C4) of the sealing plate 42A having a substantially rectangular shape. In such a configuration, a flow path resistance can be increased compared to the configuration in which the communication path 428 is substantially linearly formed.

Third Embodiment

Hereinafter, a third embodiment will be described.

In the first embodiment, the communication path 425 is linearly extended toward the hole portion 426 formed in the vicinity of the outer peripheral edge of the sealing plate 42 in the plan view, and communicates with the hole portion 426. In contrast, the third embodiment differs from the first embodiment in that the communication path meanders in the plan view.

In the following description, configurations similar to those of the first embodiment are denoted by the same reference numerals and signs, and the description thereof is omitted or simplified.

Figure 10:
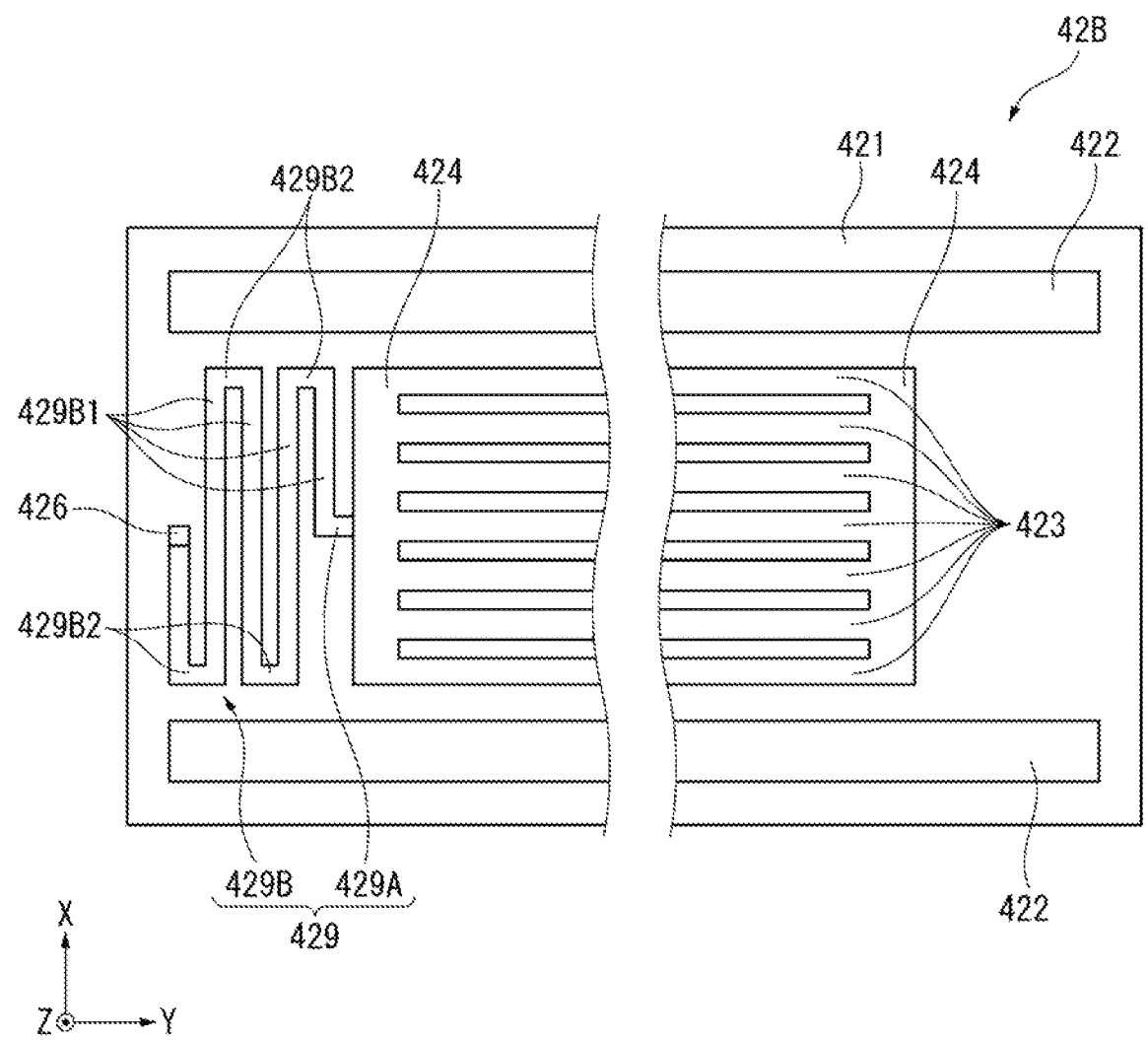
FIG. 10 is a plan view showing a schematic configuration of a sealing plate of a third embodiment.

FIG. 10 is a plan view schematically showing a sealing plate 42B as viewed from the element substrate 41 side.

A communication path 429 that communicates at one end with the coupling path 424 and communicates at the other end with the hole portion 426 is formed in the sealing plate 42B.

The communication path 429 includes a connection portion 429A that connects to the coupling path 424, and a meandering portion 429B that communicates at one end with the connection portion 429A and communicates at the other end with the hole portion 426. In the plan view, the communication path 429 is extended in a direction (Y-direction) away from the groove portion 423 overlapping the piezoelectric element 413.

The connection portion 429A is extended in the Y-direction from the coupling path 424.

The meandering portion 429B is extended in the Y-direction from the connection portion 429A toward the hole portion 426 while meandering along the X-direction and the Y-direction. That is, the meandering portion 429B includes a plurality of first extending portions 429B1 extended in the X-direction, and a plurality of second extending portions 429B2 extended in the Y-direction from the first extending portions 429B1. The first extending portion 429B1 and the second extending portion 429B2 are repeatedly formed to constitute the meandering portion 429B. In the embodiment, the X-direction dimension of the first extending portion 429B1 extended in the X-direction is larger than the Y-direction dimension of the second extending portion 429B2 extended in the Y-direction.

Operations and Advantageous Effects of Third Embodiment

In the third embodiment configured as described above, the following operations and advantageous effects can be obtained in addition to the operations and advantageous effects of the first embodiment.

The communication path 429 includes the meandering portion 429B. Therefore, compared to the case where the meandering portion 429B is absent, the path length of the communication path 429 can be lengthened, and thus the inflow of a foreign substance from the external space into the internal space 420 can be more reliably suppressed.

Moreover, the meandering portion 429B is bent at the connection position of the first extending portion 429B1 and the second extending portion 429B2. For this reason, a flow path resistance can be increased at the bent position, and thus the inflow of a foreign substance from the external space can be more effectively suppressed.

Fourth Embodiment

Hereinafter, a fourth embodiment will be described.

The fourth embodiment is configured substantially similarly to the second embodiment, but differs therefrom in that depressions and projections are formed on the coupling path or the communication path.

In the following description, configurations similar to those of the second embodiment are denoted by the same reference numerals and signs, and the description thereof is omitted or simplified.

Figure 11:
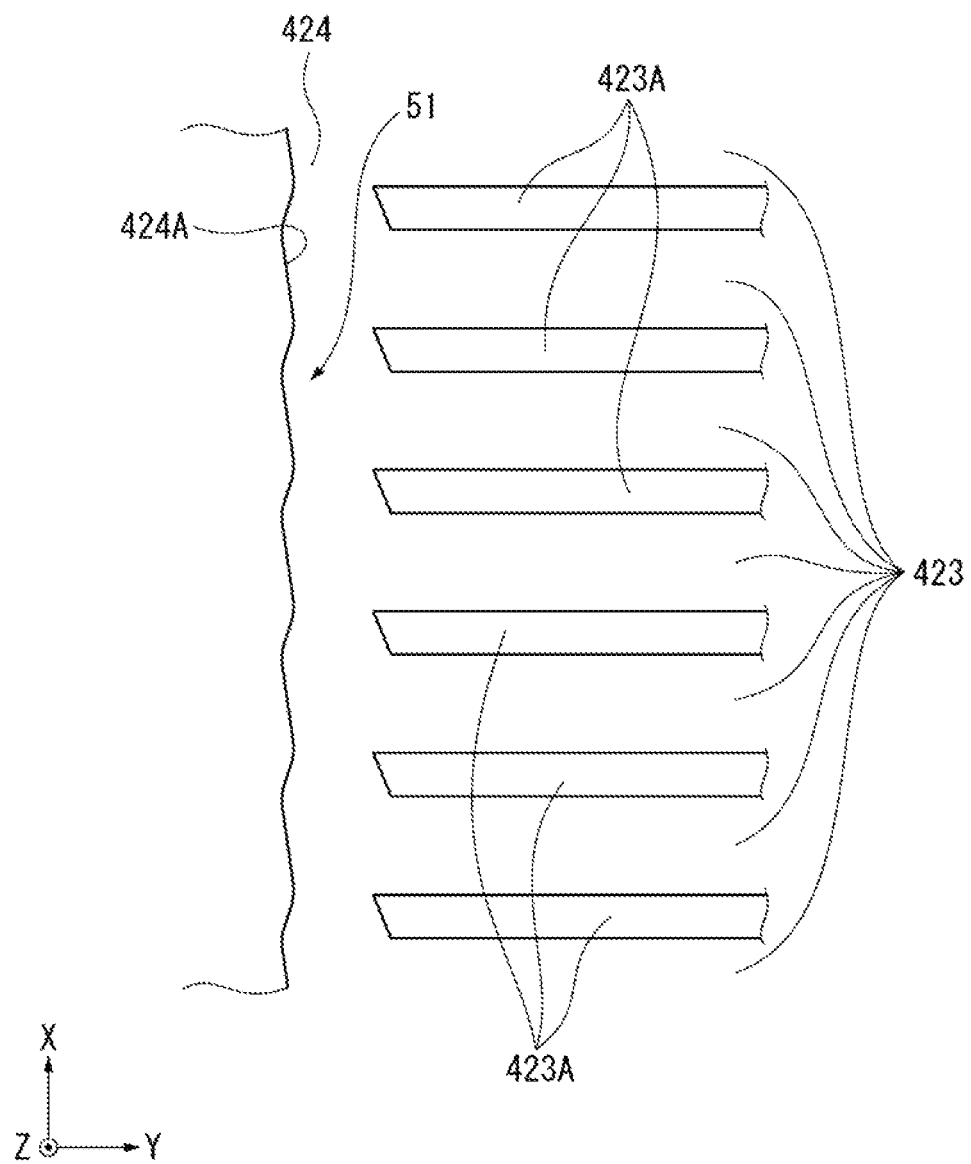
FIG. 11 is an enlarged partial plan view showing a schematic configuration of a sealing plate of a fourth embodiment.
Figure 12:
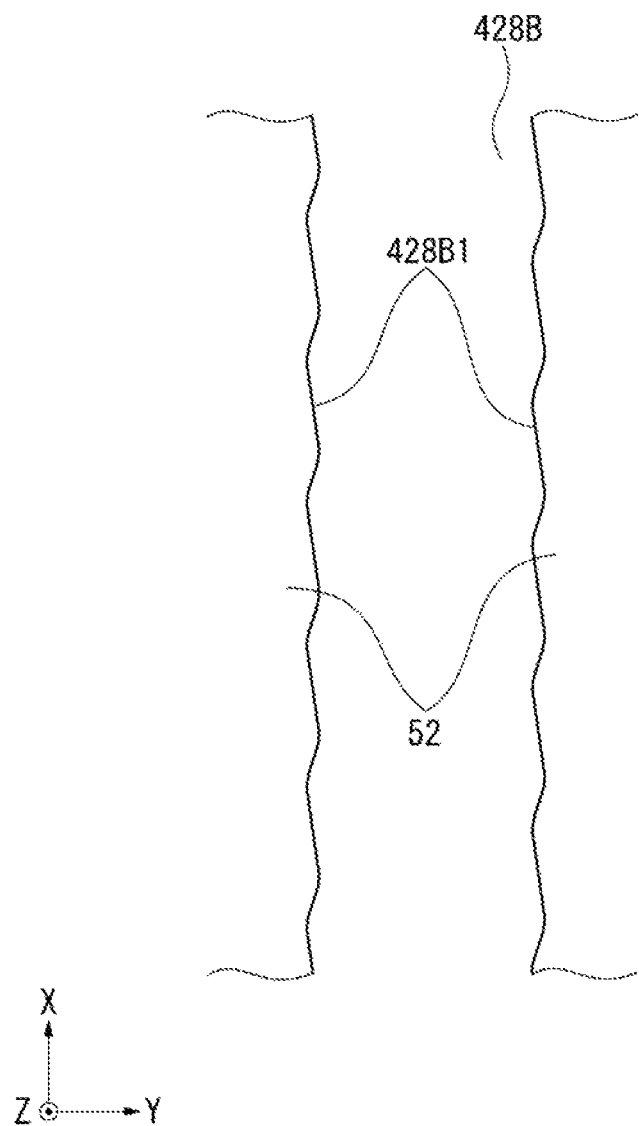
FIG. 12 is an enlarged partial plan view showing a schematic configuration of the sealing plate of the fourth embodiment.

FIG. 11 is a partial plan view showing a schematic configuration of the groove portion 423 and the coupling path 424. FIG. 12 is a partial plan view showing a schematic configuration of the second communication portion 428B.

As shown in FIG. 11, a plurality of depressions and projections 51 are formed on a coupling path inner surface 424A parallel to the ZX plane and orthogonal to the Y-direction, in the inner surfaces of the coupling path 424.

The depressions and projections 51 can be formed by, for example, carrying out anisotropic etching utilizing crystal anisotropy in performing wet etching. That is, when the sealing plate is formed using a Si substrate, a groove wall surface 423B of the groove portion 423 can be easily formed substantially flat by appropriately adjusting the surface orientation of Si crystal. Then, when the coupling path 424 is formed simultaneously with the groove portion 423, the depressions and projections 51 are formed on the coupling path inner surface 424A along the ZX plane due to a difference in etching rate based on the crystal anisotropy. As shown in FIG. 11, the depressions and projections 51 include a plurality of depressed portions and projected portions formed repeatedly at substantially constant intervals in the X-direction. The repeated intervals of the depressed portions and the projected portions are, for example, substantially the same as the arrangement intervals of the groove portions 423.

Moreover, when the crystal orientation of the Si substrate is set along the forming direction of the groove portion 423 as described above, depressions and projections are similarly formed also on a surface along the ZX plane, in the inner surfaces of the communication path 428 (see FIG. 9). That is, as shown in FIG. 12, a communication path inner surface 428B1 of the second communication portion 428B is formed along the ZX plane, and depressions and projections 52 are formed on the communication path inner surface 428B1. The depressions and projections 52 include a plurality of depressed portions and projected portions formed repeatedly at substantially constant intervals in the X-direction similarly to the depressions and projections 51. The depressions and projections 52 are similarly formed also on inner surfaces of the fourth communication portion 428D and the sixth communication portion 428F that are formed along the ZX plane.

Operations and Advantageous Effects of Fourth Embodiment

In the fourth embodiment configured as described above, the following operations and advantageous effects can be obtained in addition to the operations and advantageous effects of the first embodiment and the second embodiment.

The depressions and projections 52 are formed on the communication path inner surface 428B1 of the second communication portion 428B or on the communication path inner surfaces of the fourth communication portion 428D and the sixth communication portion 428F. A flow path resistance of the communication path 428 can be increased by forming the depressions and projections 52 on at least a portion of the inner surfaces of the communication path 428 as described above, and thus the inflow of a foreign substance can be suppressed.

Moreover, the depressions and projections 51 are formed on the coupling path inner surface 424A of the coupling path 424. In such a configuration, a flow path resistance of the coupling path 424 can be increased, and thus the inflow of a foreign substance from the outside into the internal space 420 can be suppressed.

Modified Example

The invention is not limited to the embodiments. The invention includes modifications, improvements, and configurations that are obtained by, for example, appropriately combining the embodiments, within the scope in which the advantage of the invention can be achieved.

Figure 13:
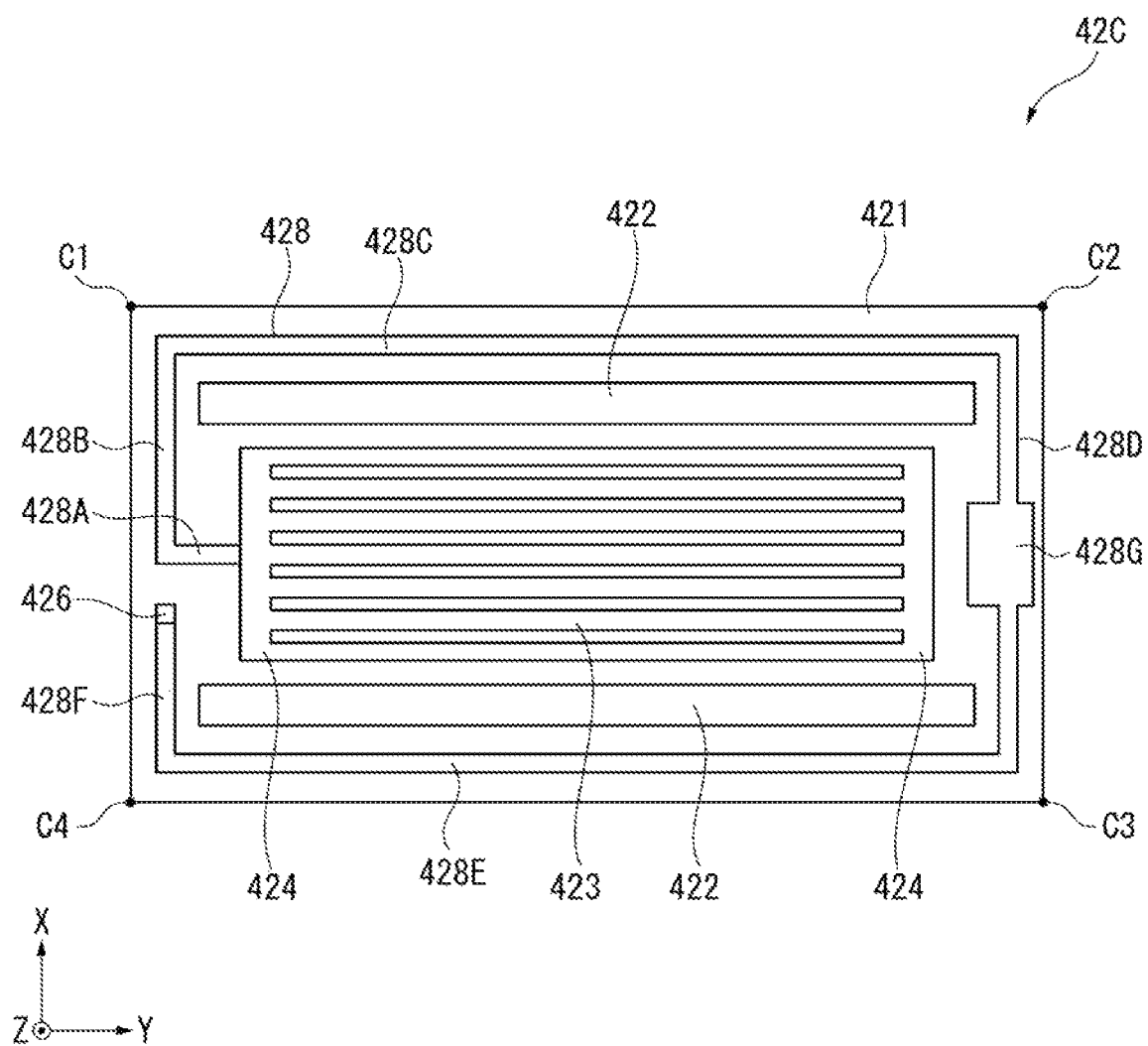
FIG. 13 is a plan view showing a schematic configuration of a sealing plate according to a modified example.

FIG. 13 is a plan view showing a schematic configuration of a sealing plate according to a modified example.

The sealing plate 42C shown in FIG. 13 is configured substantially similarly to that of the second embodiment, except that a wide portion 428G whose area in cross-section crossing the flow direction of the communication portion is increased is formed in a portion of the communication path 428. The wide portion 428G is formed so as to widen a portion of the fourth communication portion 428D. The wide portion 428G is formed at a substantially intermediate position in the communication path 428 formed along the outer periphery of the sealing plate 42C. The dimensions of the wide portion 428G in the Y-direction and the Z-direction are larger than those of the communication path 428 (the fourth communication portion 428D). That is, the cross-sectional area of the wide portion 428G in a plane parallel to the YZ plane is larger than the cross-sectional area of the communication path 428 (the fourth communication portion 428D). The wide portion 428G may be configured such that the dimension of the wide portion 428G in any of the Y-direction and the Z-direction is larger than that of the communication path 428 (the fourth communication portion 428D).

In such a configuration, a flow path resistance can be increased due to a difference in cross-sectional area between the wide portion 428G and the fourth communication portion 428D. Moreover, the wide portion 428G can function as a trap to prevent the inflow of a foreign substance from the outside, and thus the inflow of a foreign substance can be more reliably suppressed.

In the second embodiment, the communication path 428 is extended so as to substantially go around the outer periphery (the first side 421A, the second side 421B, the third side 421C, and the fourth side 421D) of the sealing plate 42C; however, the communication path is not limited to this. For example, the communication path may be extended along only one first side 421A, and connected to the hole portion 426 that is formed in the vicinity of the point C1. Moreover, the communication path may be extended along the two first and second sides 421A and 421B, and connected to the hole portion 426 that is formed in the vicinity of the second side 421B. Moreover, the communication path may be extended along the first side 421A, the second side 421B, and the third side 421C, and connected to the hole portion 426 that is formed in the vicinity of the third side 421C. Moreover, the communication path may be extended along the first side 421A, the second side 421B, the third side 421C, and the fourth side 421D, and connected to the hole portion 426 that is formed in the vicinity of the fourth side 421D.

In the third embodiment, the meandering portion 429B includes the first extending portions 429B1 and the second extending portions 429B2, which are substantially linear in the plan view, and is bent at the connection position of the first extending portion 429B1 and the second extending portion 429B2; however, the meandering portion is not limited to this. For example, the second extending portion 429B2 that connects two first extending portions 429B1 may be curved, and the two first extending portions 429B1 and the second extending portions 429B2 may be formed in an oval shape in the plan view. Moreover, also the first extending portion 429B1 is not limited to a linear shape, and may be curved.

In the embodiments, the configuration in which the plurality of groove portions 423 and the coupling path 424 have the same depth dimension (dimension in the Z-direction) has been exemplified; however, the invention is not limited to this. The groove portion 423 and the coupling path 424 may be different in depth dimension. Moreover, the plurality of groove portions 423 are not limited to the configuration in which all of the plurality of groove portions 423 have the same depth dimension, and the groove portion 423 having a different depth dimension may be included. Moreover, the groove portion 423 having a different width dimension in the X-direction may be included.

In the embodiments, the configuration in which the depth dimension of the communication path is smaller than that of the groove portion 423 and the coupling path 424 has been exemplified; however, the invention is not limited to this. For example, the depth dimension of the communication path may be the same as that of the groove portion 423 and the coupling path 424. In this case, for example, the communication path can be formed simultaneously with the groove portion 423 and the coupling path 424 by etching. Moreover, the depth dimension of the communication path may be larger than that of the groove portion 423 and the coupling path 424. Moreover, the depth dimension of the communication path may be different depending on the X-position and the Y-position.

In the embodiments, the configuration in which the cross-sectional area of the communication path 425 is made smaller than that of the coupling path 424 by reducing the depth dimension of the communication path 425 has been exemplified; however, the invention is not limited to this. For example, the cross-sectional area of the communication path 425 may be made smaller than that of the coupling path 424 by reducing the width dimension of the communication path 425.

In the embodiments, the configuration in which the coupling path and the communication path are grooves opened in the bonding surface 421 of the sealing plate has been exemplified; however, the invention is not limited to this. For example, the coupling path and the communication path may be formed inside the substrate (sealing plate) in which the first and second groove portions closed by the vibration film are formed.

In the embodiments, the communication path communicates with the groove portion 423 through the coupling path 424; however, the communication path is not limited to this. For example, the communication path may be extended from the groove portion 423.

Moreover, the groove portion 423 may be one groove portion that overlaps the array region Ar1, and the communication path may be configured so as to communicate with the groove portion 423. In this case, the opening 411C of the substrate main body 411 is formed in a rectangular shape in the plan vie, and defines the four sides of the flexible portion 412C.

As described above, even when the communication path communicates with the groove portion 423, the communication path is extended from the groove portion 423 in the direction away from the piezoelectric element 413 in the plan view. Therefore, the length dimension of the communication path can be increased irrespective of the thickness dimension of the sealing plate 42, and thus the inflow of a foreign substance into the internal space can be suppressed.

In the embodiments, the configuration in which only one communication path is formed has been exemplified; however, the communication path is not limited to this, and a plurality of communication paths may be formed. The pressure difference between the internal space and the external space can be more reliably suppressed by forming a plurality of communication paths.

In the fourth embodiment, the configuration in which the depressions and projections are formed on at least a portion of the coupling path 424 and the communication path 428, that is, on the surface along the ZX plane, has been exemplified; however, the depressions and projections are not limited to this, and may be formed on other surfaces such as the bottom surface of the groove. Moreover, the depressions and projections may be formed at any positions as long as the positions are located in at least a portion of the coupling path 424 and the communication path 428. Moreover, the depressions and projections may be formed only on the coupling path 424, or the depressions and projections may be formed only on the communication path 428.

In the embodiments, the configuration in which the hole portion 426 penetrates the sealing plate 42 in the Z-direction and includes the opening 426A opened in the bottom surface 427 has been exemplified; however, the invention is not limited to this. The opening 426A may be formed in a portion of the sealing plate 42 other than the bottom surface 427. For example, the opening 426A may be formed in a surface (side surface) of the sealing plate 42 that is parallel to the ZX plane, and the hole portion 426 may be formed so as to cause the opening 426A to communicate with the communication path 425. It is preferable that the opening 426A is formed in the bottom surface 427. With this configuration, even when, for example, a manufacturing process in which a plurality of ultrasonic devices 22 are simultaneously formed on a long Si substrate and thereafter the plurality of ultrasonic devices 22 are divided into individual pieces is carried out, the hole portion 426 can be formed in each of the ultrasonic devices 22. Hence, the occurrence of a pressure difference between the internal space and the outside can be suppressed during manufacture.

In the embodiments, the configuration has been exemplified, in which the sealing plate 42 is provided on the side of the working surface 412B (surface on the side opposite to the substrate main body 411) of the vibration film 412 on which the piezoelectric element 413 is formed, the acoustic layer 43 and the acoustic lens 44 are provided on the side of the opening surface 412A on the substrate main body 411 side, and the transmission and reception of ultrasonic waves are performed from the side of the opening surface 412A; however, the invention is not limited to this.

For example, a configuration may be employed, in which the acoustic layer 43 and the acoustic lens 44 are provided on the side of the working surface 412B of the vibration film 412, the sealing plate 42 is provided on the side of the opening surface 412A, and the transmission and reception of ultrasonic waves are performed from the side of the working surface 412B.

In this case, for example, a configuration may be employed, in which the substrate main body 411 corresponds to the substrate, the openings 411C correspond to the first groove portion and the second groove portion, and the coupling path and the communication path are formed in the substrate main body 411. On this occasion, a suppressing portion may be formed on the working surface 412B. The suppressing portion crosses the opening 411C, regulates the vibration range of the vibration film 412, and defines the position of the flexible portion 412C in the X-direction and the width dimension of the flexible portion 412C.

When the configuration is employed in which the acoustic layer 43 and the acoustic lens 44 are provided on the side of the working surface 412B of the vibration film 412, the sealing plate 42 is provided on the side of the opening surface 412A, and the transmission and reception of ultrasonic waves are performed from the side of the working surface 412B as described above, the sealing plate 42 may be bonded to the surface of the substrate main body 411 on the side opposite to the vibration film 412. In this case, the groove portion 423 formed in the sealing plate 42 is sealed by the vibration film 412 with the substrate main body 411 between the vibration film 412 and the groove portion 423. The opening 411C of the substrate main body 411 is formed in a rectangular shape in the plan view, and defines the four sides of the flexible portion 412C.

In the embodiments, the ultrasonic apparatus whose object of measurement is an organ in a living body has been exemplified as an electronic apparatus; however, the invention is not limited to this. For example, the configuration of each of the embodiments and modified example can be applied to a measuring machine whose object of measurement is any of various structures and which performs detection of a defect of the structure or inspection for aging deterioration. Moreover, the configuration of each of the embodiments and modified example can be applied similarly to, for example, a measuring machine whose object of measurement is a semiconductor package, a wafer, or the like and which detects a defect of the object of measurement.

Moreover, the configuration described in each of the embodiments and modified example can be applied to a piezoelectric device including a piezoelectric element. For example, an inkjet head that ejects an ink drop by driving the piezoelectric element can be exemplified as a configuration including the piezoelectric device. Moreover, a recording apparatus including the inkjet head can be exemplified as an electronic apparatus described in each of the embodiments and modified example.

Specifically, the inkjet head is configured to include, for example, a nozzle plate, an ink flow path forming substrate, an element substrate, and a sealing plate. A plurality of nozzles through which ink is ejected are formed in the nozzle plate. Ink chambers corresponding to the nozzles and filled with ink, ink flow paths for distributing ink to the ink chambers, and the like are formed in the ink flow path forming substrate. The nozzle plate is provided on one surface of the ink flow path forming substrate. The element substrate is provided on a surface of the ink flow path forming substrate opposite to the one surface. The element substrate is provided with piezoelectric actuators including the vibration film and the piezoelectric elements at positions corresponding to the ink chambers. The sealing plate is provided on the element substrate on the side opposite to the ink flow path forming substrate. In the inkjet head configured as described above, the ink inside the ink chamber is ejected through the nozzle by driving of the piezoelectric element. Also, a configuration may be employed, in which the ink flow path and the ink chamber are formed in the element substrate and the nozzle plate is provided on the element substrate.

In addition, a specific structure in implementing the invention may be configured by appropriately combining the embodiments and modified example within the scope in which the advantage of the invention can be achieved, or may be appropriately changed to another structure or the like.

The entire disclosure of Japanese Patent Application No. 2016-239751 filed Dec. 9, 2016 is expressly incorporated by reference herein.

What is claimed is:

1. An ultrasonic device comprising:
   a substrate including a first groove portion and a second groove portion in a first surface;
   a vibration film provided on the first surface and closing the first groove portion and the second groove portion;
   a first piezoelectric element provided on the vibration film and overlapping the first groove portion in a plan view as viewed in a thickness direction of the substrate; and
   a second piezoelectric element provided on the vibration film and overlapping the second groove portion in the plan view, wherein
   the substrate is provided with a third groove portion coupling the first groove portion to the second groove portion,
   the substrate is provided with a fourth groove portion extending in a direction away from the first piezoelectric element and the second piezoelectric element in the plan view and coupled to the third groove portion, and
   a hole portion coupling a second surface of the substrate that is opposed to the first surface to the fourth groove portion is provided.

2. The ultrasonic device according to claim 1, wherein the cross-sectional area of the fourth groove portion is smaller than the cross-sectional area of the third groove portion.

3. The ultrasonic device according to claim 1, wherein an inner surface of the fourth groove portion includes a plurality of depressions and projections.

4. The ultrasonic device according to claim 1, wherein an inner surface of the third groove portion includes a plurality of depressions and projections.

5. The ultrasonic device according to claim 1, wherein the fourth groove portion is further extended along an outer periphery of the substrate.

6. The ultrasonic device according to claim 1, wherein the fourth groove portion includes a meandering portion meandering in the plan view.

7. An ultrasonic device comprising:
   a substrate including a first groove portion and a second groove portion in a first surface;
   a vibration film provided on the first surface and closing the first groove portion and the second groove portion;
   a first piezoelectric element provided on the vibration film and overlapping the first groove portion in a plan view as viewed in a thickness direction of the substrate; and a second piezoelectric element provided on the vibration film and overlapping the second groove portion in the plan view, wherein the first groove portion and the second groove portion extend in a first direction and are adjacent to each other in a second direction crossing the first direction, the substrate is provided with a third groove portion extending in the second direction and coupling one end side of the first groove portion to one end side of the second groove portion, the substrate is provided with a fourth groove portion extending in a direction away from the first piezoelectric element and the second piezoelectric element in the plan view and coupled at one end side to the third groove portion, and a hole portion coupling a second surface of the substrate that is opposed to the first surface to the other end side of the fourth groove portion is provided.

8. An ultrasonic apparatus comprising:

a substrate including a first groove portion and a second groove portion in a first surface;

a vibration film provided on the first surface and closing the first groove portion and the second groove portion;

a first piezoelectric element provided on the vibration film and overlapping the first groove portion in a plan view as viewed in a thickness direction of the substrate;

a second piezoelectric element provided on the vibration film and overlapping the second groove portion in the plan view; and a control unit controlling the first piezoelectric element and the second piezoelectric element, wherein the substrate is provided with a third groove portion coupling the first groove portion to the second groove portion, the substrate is provided with a fourth groove portion extending in a direction away from the first piezoelectric element and the second piezoelectric element in the plan view and coupled to the third groove portion, and a hole portion coupling a second surface of the substrate that is opposed to the first surface to the fourth groove portion is provided.

* * * * *